United States Patent [19]
Yonemura

[11] Patent Number: 5,123,738
[45] Date of Patent: Jun. 23, 1992

[54] STANDARD SUBSTANCE FOR OPTICAL CALIBRATION AND METHOD OF MAKING SAME

[75] Inventor: Masaru Yonemura, Kobe, Japan

[73] Assignee: TOA Medical Electronics Co., Ltd., Kobe, Japan

[21] Appl. No.: 385,893

[22] Filed: Jul. 26, 1989

[30] Foreign Application Priority Data

Dec. 15, 1988 [JP] Japan .................. 63-317219

[51] Int. Cl.⁵ ............................... G01J 1/02
[52] U.S. Cl. .................................. 356/243
[58] Field of Search .......................... 356/243

[56] References Cited

U.S. PATENT DOCUMENTS 4,322,164  3/1982  Shan et al. ............... 356/243

FOREIGN PATENT DOCUMENTS 2022282  12/1979  Japan ................... 356/243
57-41688  9/1982  Japan .

Primary Examiner—Samuel Turner
Attorney, Agent, or Firm—Morrison Law Firm

[57] ABSTRACT

A standard substance for optical calibration is produced by mixing a proportion of a scattering substance with a first silicone liquid. The optical properties of the first liquid are measured and a further amount of the first liquid is added to the original mixture to provide a desired optical property. Then, the mixture is further mixed with a second silicone liquid which initiates a curing process. The final mixture is poured into a transparent vessel for curing. The transparent vessel, with the cured final mixture inside, is useful as a standard substance for calibration of an optical equipment. A technique for calculating the proportions of the mixtures is disclosed.

10 Claims, 2 Drawing Sheets

FIG. 1
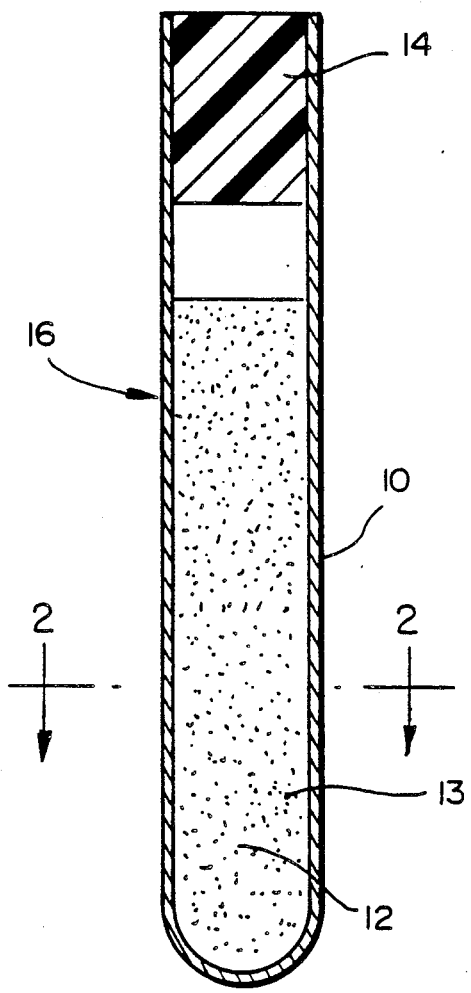
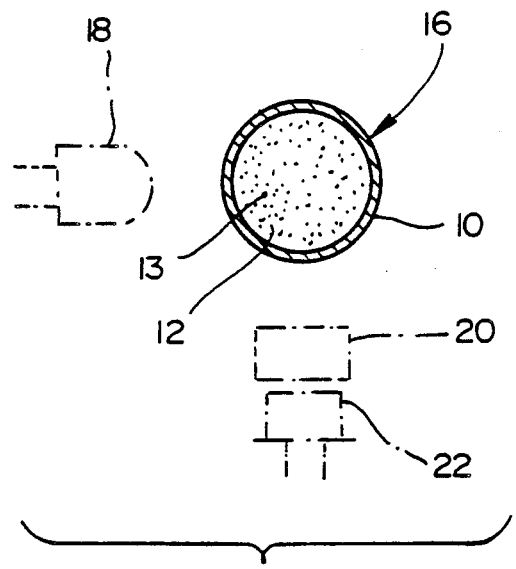
FIG. 2

STANDARD SUBSTANCE FOR OPTICAL CALIBRATION AND METHOD OF MAKING SAME

BACKGROUND OF THE INVENTION

The present invention relates to optical calibration and, more particularly, to a standard substance for calibration of an optical measurement device for measuring optical transmission and scattering.

Optical measurement devices exist for analyzing a sample of a material based on the transmission or scattering of light passing therethrough. For example, a device is known which measures the coagulation time of directing a light through a mixture of blood plasma and a sample chemical. Coagulation is detected by a change in the light-scattering property of the mixture due to increased turbidity when fibrinogen in the blood plasma is converted to fibrin during coagulation.

Such optical measurement devices require calibration to maintain their accuracy under varying conditions over time. One way of calibrating such devices employs a standard substance having known properties of light transmission and scattering. One possible standard substance includes a sample of the material which is to be measured. In the case of the coagulation-time measurement apparatus described above, the standard substance is a mixture of blood plasma and chemical which is to be measured. This has not proven to be a successful technique since such a sample lacks long-term stability and requires frequent adjustment of the measurement device.

Other standard substances include, for example, agar, gelatin, acrylamide gel, chitin and geldium jelly. The turbidity of the above substances can be adjusted by changing the concentration of the ingredients. The turbidity of agar can be changed by changing the concentration of agarose, which is one of its main ingredients. However, since agar, as well as the remainder of the above candidate standard substances, contain a high concentration of water, care must be taken to avoid evaporation of the water, and the resulting change in turbidity. This generally requires a closely plugged container.

In addition, the above standard substances are gels. As is well known, the lattice structure of most gels is unstable and has no resistance to shaking. Thus, long-term stability is difficult to maintain.

A further problem with the above prior substances is that they contain organic substances which are nutritious to bacteria. For example, agarose is an organic substance that is hospitable to bacteria. Bacteria contamination is a further threat to long-term stability.

Because of the above problems with organic gels, it appears desirable to employ an inorganic standard substance for calibration of an optical detector.

One type of inorganic standard substance includes a glass standard scattering substance such as, for example, that disclosed in Japanese Examined Patent Publication No. 57-41688, published in 1982. This material is made by mixing a small quantity of impurities to silicon oxide. The mixture is melted and baked at a suitable temperature. As a result of the melting and baking, the impurities form small nuclear crystals. Thus is formed a glass in a boric acid phase. The resulting glass scattering substance is placed in a transparent container. Gaps in the container are filled with a liquid.

This technique has the disadvantage that the process for making the glass standard is complicated, and the resulting device is not completely stable. Several attempts are typically required to determine the amount of turbidity-enhancing substance to add. The resulting glass must be melted and formed to conform to the shape of the light-measuring device. Consequently, the device is generally larger than desired and more costly. Also, since the device is stored in a container, it is difficult to maintain the scattering substance stably in the container. Hence its optical stability is also difficult to maintain.

Alternatively, the glass standard substance can be formed as a hollow glass tube. The amount of scattering can be varied by changing the inner diameter of the tube. The amount of scattering is increased by making the inner diameter smaller, and is decreased by making the inner diameter larger.

The optical properties of this device are degraded if any portion of the outer or inner surface is deformed. In addition, such a glass tube tends to shrink over time, with resulting optical instability.

OBJECTS AND SUMMARY OF THE INVENTION

It is an object of the invention to provide a standard substance for optical calibration, and a method for making same that overcome the drawbacks of the prior art.

It is a further object of the invention to provide a method for making a standard substance wherein scattering materials are added to a low-viscosity material which is then hardened to a high-viscosity or solid material.

It is a still further object of the invention to provide a method for making a standard substance wherein a first silicone resin is mixed with a turbid substance. The concentration of turbid substance is adjusted, if necessary, by adding additional first silicone resin. Then a second silicone resin, which acts as a hardener, is added to the mixture. The concentration of turbid substance in the first silicone resin is chosen such that, after the second silicone resin is added, and the mixture is cured, a resulting turbidity of the cured mixture is attained.

It is a still further object of the invention to provide a standard substance for optical calibration, which is produced by a simplified process, does not have liquids which can leak out, and which has good resistance to shaking and corrosion.

Briefly stated, the present invention provides a standard substance for optical calibration that is produced by mixing a proportion of a scattering substance with a first silicone liquid. The optical properties of the first liquid are measured and a further amount of the first liquid is added to the original mixture to provide a desired optical property. Then, the mixture is further mixed with a second silicone liquid which initiates a curing process. The final mixture is poured into a transparent vessel for curing. The transparent vessel, with the cured final mixture inside, is useful as a standard substance for calibration of an optical equipment. A technique for calculating the required mixture is disclosed.

According to an embodiment of the invention, there is provided a standard substance for optical calibration comprising: a transparent container, a cured transparent silicone in the transparent container, an amount of fine particles scattered generally uniformly through the cured transparent silicone, and the amount being effective to produce a desired optical property.

According to a feature of the invention, there is provided a process for producing a standard substance for optical calibration, comprising: adding an amount of fine particles to a first silicone liquid, dispersing the fine particles in the first silicone liquid to produce a first mixture, measuring at least one optical property of the first mixture, adding an additional amount of the first silicone liquid to the first mixture to produce a second mixture having a desired value of the at least one optical property, adding a second silicone liquid to the second mixture, mixing second silicone liquid and the second mixture to produce a uniform third mixture, the second silicone liquid being of a type effective to initiate curing of the third mixture, pouring the third mixture into a transparent container, and curing the third mixture in the transparent container to produce the standard substance.

According to a further feature of the invention there is provided a standard substance produced by the method of the preceding paragraph.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 1 is a cross section of a standard substance according to an embodiment of the invention.

FIG. 2 is a cross section taken along A—A in FIG. 1, and showing external optical elements in dash-dot lines.

DETAILED DESCRIPTION OF THE PREFERRED EMBODIMENT

Figure 3:
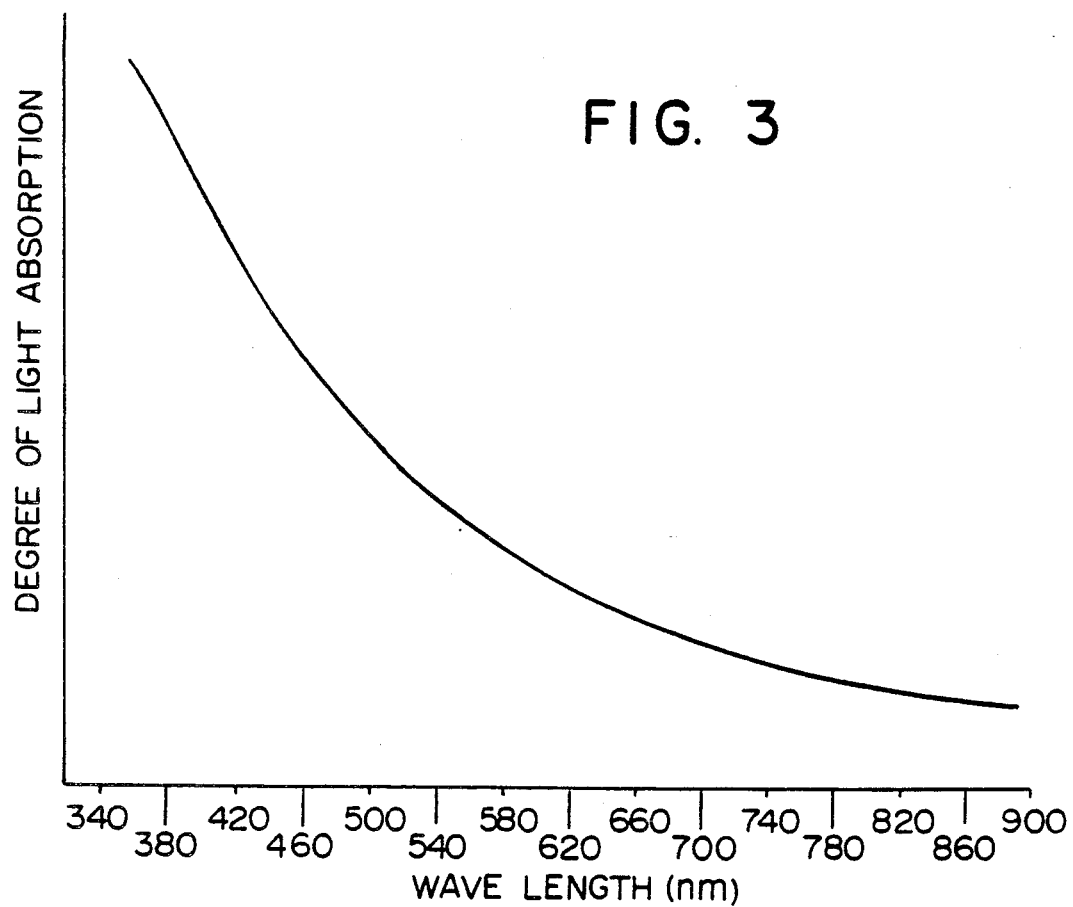
FIGS. 3 and 4 are curves to which reference will be made in describing the optical properties of the standard substance according to the present invention.

Referring to FIG. 1, a standard substance according to the invention includes a transparent container 10 with a closed bottom and having therein a cured transparent silicone 12 with a predetermined concentration of fine particles 13 uniformly dispersed therein. A plug 14 closes a top of transparent container 10.

In the preferred embodiment, when uncured, silicone 12 is first and second separated, transparent, low-viscosity liquids. For present purposes, the first and second liquids are interchangeable. When the first and second liquids are mixed, curing takes place of a time that depends on the types and concentrations of the materials and on the temperature.

The preferred process for preparing the material includes the following steps:
1) adding fine particles in the first liquid (either liquid is satisfactory),
2) dispersing and scattering the fine particles in the first liquid,
3) deaerating the mixture by application of low pressure,
4) pouring the deaerated mixture into transparent container 10,
5) measuring the optical properties of the deaerated mixture,
6) adding a first quantity of the first liquid to a second quantity of the mixture of step 3), if necessary, to obtain a first desired optical property,
7) adding a third quantity of a second liquid to the mixture of step 6),
8) mixing the ingredients in step 7) to produce a uniform mixture;
9) deaerating the uniform mixture by application of low pressure,
10) pouring the deaerated uniform mixture into transparent container 10,
11) hardening the uniform mixture of step 10) to produce silicone 12 having particles 13 uniformly dispersed therein, and
12) the desired optical property in step 7) including obtaining of a second desired optical property at the end of step 11).

One skilled in the art will recognize that some applications may not require deaeration of the mixtures. Also, other types of silicone may be used besides the two-fluid type. A type of transparent silicone that is hardened by irradiation, moisture, heat, or other effect, may be substituted without departing from the spirit and scope of the invention.

In the preferred embodiment, the cured transparent silicone is produced by the reaction of a vinyl radical and a SiH radical under the influence of a Pt catalyst.

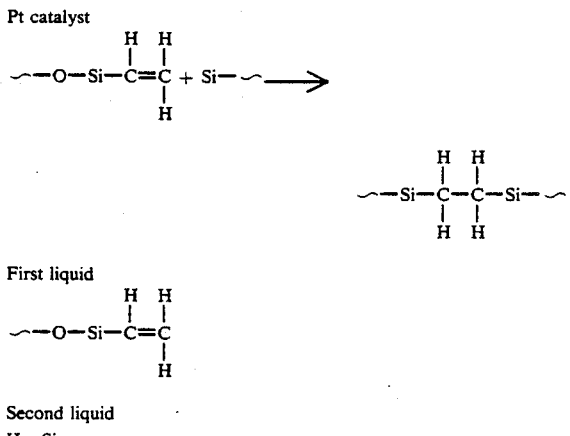

As noted above, either liquid may be substituted for the other. The Pt catalyst may be contained in either the first or second liquids.

The material used for particles 13 may be of any convenient type. It has been discovered that many coloring materials are chemical substances that change color when irradiated with light. Such coloring materials are not ideal for the present invention. Pigments consisting of fine particles are found to be satisfactory, provided they have a required small size, uniformity, and long-term stability required in the present application.

One pigment that appears to be satisfactory is titanium dioxide. However, it is understood that titanium dioxide emits electrons when excited by radiation. Thus it is unstable optically. The particles of titanium dioxide may be coated with, for example, alumina, to avoid instability from this cause. This yields coated particles having average diameters of about 0.25 micrometers.

Other types of particles and/or coatings may also be used. For example, coatings of silica or zinc may be satisfactory in some applications.

Referring now to FIG. 2, optical measurement of scattering of light in a standard substance 16 may be performed by positioning a light emitting element 18 such as, for example, a lamp or a light-emitting diode, at one side of transparent container 10. A light receiving element 22 is positioned at about 90 degrees about standard substance 16 from light emitting element 18. A filter 20 is optionally provided to limit the wavelengths of light reaching light receiving element 22. It will be understood that a signal generated by light receiving element 22 is applied to a conventional photoelectric converter, which provides the final output. Since such a photoelectric converter is conventional, and well known to those skilled in the art, further discussion thereof is omitted. As depicted, light receiving element 22 receives light that is scattered by particles 13 to an angle of 90 degrees from the direct path through silicone 12. One skilled in the art will recognize that a corresponding absorption measurement can be performed by relocating filter 20 and light receiving element 22 in a direct line with light emitting element 18 on the opposite side of standard substance 16. When the apparatus of FIG. 2 is used for blood-coagulation measurement, light emitting element 18 is preferably a red optical source, and more preferably a red light emitting diode.

Referring now to FIG. 3, a curve relates the amount of light absorption to the wavelength of light for the standard material described above. It is of note that the curve is smooth. This indicates that a single type of particle is useable over a wide range of optical wavelengths.

Figure 4:
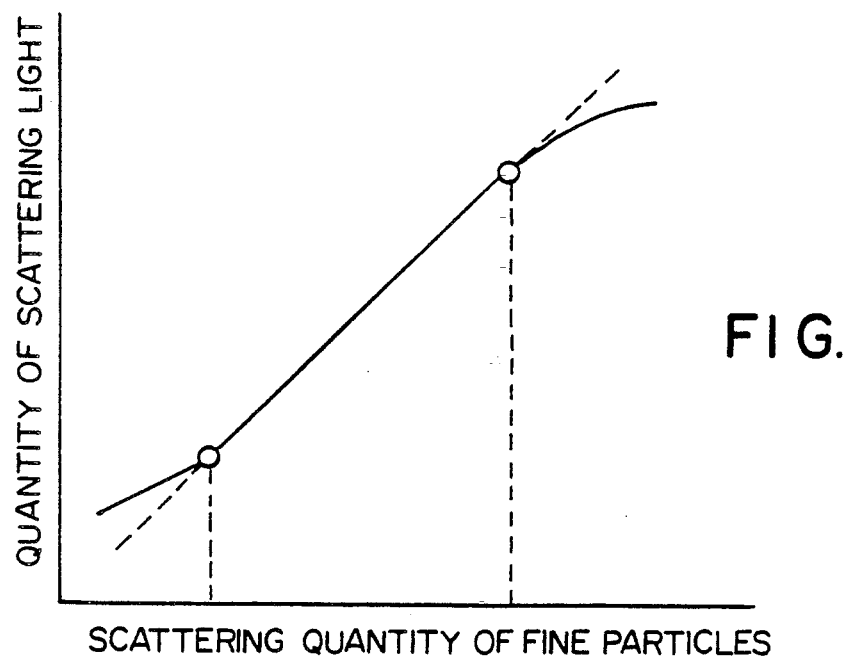

Referring now to FIG. 4, a curve relates the amount of light scattered to the quantity of scattering particles in the final cured mixture. It will be noted that, over a substantial range, the curve is linear. Accordingly, it is possible to predict, with good accuracy, the scattering effect that will occur from a predetermined increase or decrease in the amount of scattering particles in the final cured mixture. This curve can then relate the amount of additional plain first liquid to add to the first mixture to attain the first optical property based on a single measurement of the optical properties of the first mixture after deaeration. In addition, this curve further makes it possible to predict the amount of first liquid to add in step 6) above so that, after the second liquid is added, and the final mixture is cured, it will result in the second desired optical property (the final optical property of the cured material).

A first example of the process for producing the standard substance is described in more detail below:

1) 30 ml of the first silicone liquid is poured into a beaker.

One pharmaceutical spoon of particles of titanium dioxide is poured into the first liquid. The particles are dispersed uniformly throughout the first silicone liquid using a suitable agitator for at least a few minutes, and preferably overnight.

2) Larger and non-uniform particles may be removed from the mixture by letting the mixture stand for several hours, or by subjecting the mixture to 1500 G in a centrifuge for about 15 minutes.

3) The upper portion of the gravity-separated or centrifuged mixture is decanted to select the finer, and more uniform particles, dispersed in the first liquid.

4) The decanted portion is deaerated at pressure of about 50 Torr, and preferably less than about 300 Torr for about 5 minutes.

5) Part of the decanted deaerated liquid is poured into a second test tube.

6) The optical scattering properties of the material in the second test tube are measured.

7) An additional quantity of the first liquid, not containing the scattering particles, in an amount sufficient to result in the desired final optical properties of the cured material, is added to the decanted deaerated liquid. The amount of the first liquid to be added is guided by the relationship between light scattering and the quantity of fine particles per unit volume shown in FIG. 4. That is, over some, the light scattering is linearly related to the quantity of fine particles per unit volume in the mixture. This relationship permits adjustment of the concentration of particles per unit volume based on a single scattering measurement. If the measured amount of scattered light in the first liquid is "A", the desired scattered light in the final standard substance is "B", the first and second liquids are both transparent, in the linear range of FIG. 4, the following relationship may be used to determine the amounts of the first liquid (with particles) and additional liquid to be mixed.

A/B = slope of linear portion of FIG. 4.

x = the amount of the first liquid whose optical properties were measured y = the additional quantity of liquid (without particles) added in this step z = the quantity of second liquid added to begin curing the silicone The final optical properties can be found from the equation:

$$A/B = (x+y+z)/x$$

$$A\,x = (x+y+z)B$$

If the amounts of first and second liquid are equal, then $z = x+y = a$ and $A\,x = 2aB$ These equations can be solved for x and y, and thus for z.

8) The quantity "a" of the first liquid in step 7) is added to an equal quantity of the second liquid and agitated until uniformly mixed.

The final mixture is deaerated at a pressure of 50 Torr for five minutes. The final mixture begins to harden immediately, so that steps 8) and 9) must be carried out quickly. Cooling of the mixture may be employed to delay hardening.

10) The deaerated mixture of step 9) is collected in an injector and injected in a test tube. Care is taken to avoid air bubbles.

11) The test tube is heated to expedite hardening. The hardening temperature used depends on the silicone. High temperatures are desirable because of the reduced hardening time. Too high a temperature may cause expansion and then shrinking when the tube cools to room temperature. This can cause cracking. One type of silicone can be hardened by baking for one hour at 70 degrees C. Hardening may also be completed at room temperature.

12) The upper opening of the test tube is sealed by an epoxy adhesive plug to protect the cured silicone in the test tube.

A second example of the process for producing the standard substance is described in more detail below:

A silicone liquid (Product No. SE1890) produced by Toray Silicone Co. Ltd. includes a first liquid "A" and a second liquid "B" to be mixed in equal quantities to initiate curing. A pigment (Product No. JR-600A) produced by Teikoku Kako Co., Ltd. is a rutile type titanium oxide.

1) 100 milliliters of liquid A is mixed in a beaker with 30 microliters of pigment and agitated all night by a polytetrafluoroethylene chip agitator.

The mixture from step 1) is centrifuged for 15 minutes at 1500 G.

The upper half of the liquid from step 2) is transferred to another beaker.

4) The liquid from step 3) is deaerated for five minutes at 50 Torr.

5) The deaerated liquid from step 4) is transferred to a new test tube.

6) The amount of scattered light is measured by a blood coagulation measuring device, model No. CA-4000 made by Toa Iyou Denshi Co., Ltd. The measured value obtained by Analog/Digital conversion was 350. The desired value was 90.

7) By the method in example 1, the amount of liquid from step 5) is 51.4 milliliters and the additional amount of liquid A to be added is 48.6 milliliters.

8) The 100 milliliters of mixture from step 7) is mixed with 100 milliliters of liquid B to initiate the curing process. This mixture is agitated.

9) The mixture from step 8) is deaerated for five minutes at 50 Torr.

10) The deaerated mixture from step 9) is sucked into an injector and injected into a test tube, taking care to avoid introduction of air bubbles.

11) The test tube from step 10 is heated for one hour at 70 degrees C. For this type of silicone, it is believed that curing should be performed at a temperature between 50 and 90 degrees C. Temperatures greater than 100 degrees are believed to cause cracking of the cured silicone.

12) The opening in the test tube is sealed with conventional epoxy adhesive.

The above second example was used to produce a number of test tubes. Each of the test tubes exhibited the same optical properties.

Other silicone products which may be used include Product Nos. SE1885A/B, SE 1886 and SE1887. Their curing conditions are slightly different. Preferably, SE1885A/B, SE1886 and SE1887 may be heated for 30 minutes at 70 degrees C, 30 minutes at 120 degrees C (or 60 minutes at 100 degrees C), and 30 minutes at 70 degrees C (or 120 minutes at 50 degrees C), respectively.

As discussed in the background of the invention, the standard substance produced according to the method of this invention provides a light scattering substance similar to blood plasma. However, it has a broad scope beyond the specific example given in the foregoing. For example, the invention may be applied to producing an optical filter having desired optical qualities. Conventionally, light refraction and wave length have been measured using a glass filter. The standard substance of the present invention may provide preferred optical properties to such a filter by changing the quantity of pigment.

In biological and chemical fields, measurements are made at a plurality of wavelengths to determine the ingredients, or the purity of a substance. Since the optical properties of the present standard substance are stabilized over a broad range of wavelengths, and remain stable for a long time, optical adjustment can be performed at a plurality of wavelengths.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. An standard substance for optical calibration comprising:
    a transparent container;
    a cured transparent silicone in said transparent container;
    an amount of fine particles scattered generally uniformly through said cured transparent silicon;
    a surface of each of said fine particles being coated; and
    said amount being effective to produce a desired optical property.

2. A standard substance according to claim 1, wherein said transparent container is a tubular container having a closed bottom.

3. A standard substance according to claim 2, further comprising a plug closing a top of said tubular container.

4. A method for producing a standard substance for optical calibration, comprising:
    (a) adding to a first silicone liquid an amount of fine particles, a surface of each which is coated, then agitating and scattering said fine particles in the liquid;
    (b) centrifuging the liquid prepared by step (a);
    (c) collecting from the liquid prepared by step (b) a liquid portion in which the fine particles are scattered uniformly, and deaerating the collected liquid portion under a low pressure;
    (d) measuring at least one optical property of said container and said liquid portion;
    (e) adding a predetermined amount of the first silicone liquid to the liquid portion prepared in step (c) so that the liquid portion prepared by step (d) can be provided with a desired value of the optical property;
    (f) adding a second silicone liquid to a liquid prepared by step (e) and agitating the two liquids to produce a mixture thereof;
    (g) deaerating the liquids mixture prepared by step (f) under a low pressure; and
    (h) pouring the mixture prepared by step (g) in the transparent container and the curing said mixture thereby to provide said standard substance.

5. A method according to claim 4, wherein the liquid of step (a) is centrifuged to separate larger ones of said fine particles, and the collecting of step (c) is effected by decanting a portion of said first liquid to include substantially smaller ones of said fine particles.

6. A method according to claim 4, wherein the deaerating of steps (c) and (g) are effected at a pressure of about 50 Torr.

7. A method according to claim 4, wherein said at least one optical property is a scattering.

8. A method according to claim 4 wherein the amount of the first silicone liquid added to said liquid portion is equal to that of said liquid portion.

9. A method according to claim 4, wherein said fine particles include titanium dioxide.

10. A method according to claim 9, wherein the particle coating is a material selected from one of alumina, silica and zinc.

* * * * *